United States Patent
Holmes (10) Patent No.: US 7,089,047 B2
(45) Date of Patent: Aug. 8, 2006

(54) FAT DEPTH SENSOR

(75) Inventor: Wayne Stephen Holmes, Auckland (NZ)

(73) Assignee: Industrial Research Limited, Auckland (NZ)

(*) Notice: Subject to any disclaimer, the term of this patent is extended or adjusted under 35 U.S.C. 154(b) by 233 days.

(21) Appl. No.: 10/173,226

(22) Filed: Jun. 13, 2002

(65) Prior Publication Data

US 2003/0013954 A1 Jan. 16, 2003

Related U.S. Application Data

(63) Continuation of application No. PCT/NZ00/00249, filed on Dec. 13, 2000.

(30) Foreign Application Priority Data

Dec. 13, 1999 (NZ) ................................ 501765

(51) Int. Cl.
*A61B 5/00* (2006.01)
(52) U.S. Cl. ........................ 600/430; 128/920
(58) Field of Classification Search ................ 600/407, 600/430; 128/920
See application file for complete search history.

(56) References Cited

U.S. PATENT DOCUMENTS

| 4,226,540 A | 10/1980 | Barten et al. |
| 4,359,056 A | 11/1982 | Carlson |
| 5,829,437 A | 11/1998 | Bridges |

FOREIGN PATENT DOCUMENTS

| GB | 2313969 | 12/1997 |
| WO | WO 82/00403 | 2/1982 |

OTHER PUBLICATIONS

Derwent Abstract Accession No. 87-055845/08 (As USSR Radio Eltrn) Jul. 7, 1986 (Abstract Only).

*Primary Examiner*—Ruth S. Smith
(74) *Attorney, Agent, or Firm*—Fish & Richardson P.C.; Stephanie Seidman

(57) ABSTRACT

A non-invasive sensor suitable for measuring the depth of fat in animal tissue is described, the sensor generating and transmitting focussed discrete narrow band microwave signals into the tissue, receiving reflected microwave signals from the tissue and providing magnitude and phase information of the reflected microwave signals for a processor to compute a value of the fat depth within the tissue.

22 Claims, 3 Drawing Sheets

FAT DEPTH SENSOR

TECHNICAL FIELD

This application claims the benefit of priority under 35 U.S.C. §120 as a continuation of PCT Application No. PCT/NZ00/00249, filed Dec. 13, 2000 (published in English on Jun. 14, 2001 as WO 01/42737), which under 35 U.S.C. §119, claims priority to New Zealand Patent Application No. 501765, filed Dec. 13, 1999, both of which are incorporated by reference herein in their entirety.

This invention relates to a method and apparatus for determining the properties of animal tissue and in particular, but not exclusively to a method and apparatus of determining the thickness of a layer of fat on meat.

BACKGROUND OF THE INVENTION

The meat industry is becoming increasingly automated with the goal of becoming more efficient. Automated accurate measurement of the properties of animal tissue is therefore important to ensure efficient operation.

In particular, the accurate measurement of the composition and structure of meat carcasses, including fat depth, bone location and muscle thickness, is typically required. The measurement process is preferably non-contact to allow easier and faster measurement and assist in avoiding problems with contamination and cleaning.

Electromagnetic sensors, in particular microwave sensors have been used to detect the properties of animal tissue. Typical problems associated with the use of microwave energy include the need to focus the energy into a relatively small area or voxel, accounting for the different permittivity between different tissue samples, inaccuracies due to surface variation and the requirement for a robust sensor.

Known methods for focussing electromagnetic radiation into a voxel include the use of lenses, reflectors and synthetic aperture methods. These focus the radiation onto a specific area of the tissue and a measurement is taken of the reflected or scattered radiation. Different materials within the tissue are then detected by the energy of the reflected waves.

Traditionally, wide band signals have been used for the detection of the properties of tissue in order to obtain a required resolution. These may then be analysed using Fourier Transform and spectral estimation techniques. A disadvantage of using wide band signals is the generation of numerous spurious reflections and the requirement to use more complex and costly equipment capable of generating a wide range of frequencies. Also, the swept frequency range can not be reduced without sacrificing resolution in the detected signals. Furthermore, the generation and detection of a wide band signal requires relatively expensive equipment in comparison to narrow band systems. Problems are also encountered when attempting to measure the thickness of fat tissue as it is necessary to resolve the position of the small reflection that arises from the air-fat interface from the much larger and swamping reflection from the fat-meat interface.

The widely used Fast Fourier Transform Technique, when used over a limited bandwidth gives rise to significant errors for relatively minor errors in phase if unknown incidental scatterers are unaccounted for. Therefore, the position and response of these incidental scatterers must be determined for accurate measurement. This is acceptable only if long multiple path scatter is ignored. Spectral estimation techniques are a known method of accounting for the incidental scatterers. However, the computational burden of spectral estimation techniques is relatively expensive, requiring relatively high performance processors and therefore is not well suited to a harsh environment, due to lack of robustness.

OBJECT OF THE INVENTION

It is thus an object of the present invention to overcome or alleviate problems in tissue sensors at present, or at least to provide the public with a useful choice.

Further objects of the present invention may become apparent from the following description given by way of example only and with reference to the accompanying drawings.

SUMMARY OF THE INVENTION

According to one aspect of the invention there is provided a non-invasive sensor suitable for measuring the depth of fat in animal tissue, the sensor including:

microwave signal generation and transmission means adapted to generate and transmit microwave signals into the tissue;

focusing means adapted to focus the microwave signals onto a predetermined focal point;

control means adapted to control the microwave signal generation and transmission means to transmit, in use, at least three discrete narrow band microwave signals into the tissue;

receiving means adapted to receive reflected microwave signals from the tissue and provide magnitude and phase information of the reflected microwave signals; and processing means for receiving the magnitude and phase information provided by the receiving means and compute a value suitable for identification of the fat depth within the tissue.

Preferably, the microwave generation and transmission means generates and transmits microwave signals in the X-band.

Preferably, the receiving means includes a six port reflectometer.

Preferably, the focussing means includes a lens system.

Preferably, the processing means is programmed to compute the reflection coefficient of received microwave signals.

Preferably, the processing means is programmed to compute the phase of the received microwave signals from the reflection coefficient.

Preferably, the processing means is programmed to compute the electrical length ($d_e$) of the fat and permittivity ($\epsilon_r$) of the tissue by computing the values of electrical length and permittivity that minimise the error function $$\sum_{i=1}^{N} \left[ \tan^2 \frac{\theta_i}{2} - \frac{1}{\epsilon_r} \tan^2 \left[ \frac{2\pi f_1 \cdot d_e}{c} \right] \right] = 0$$

or is programmed to perform an equivalent computation, wherein $\theta_i$ is the phase of the received microwave signals, $f_1$ is the frequency of the received signals or frequency of the transmitted signal, c is speed of the microwave signals and N is the number of discrete narrow band signals transmitted into the tissue for the purposes of the measurement.

Preferably, the processing means is programmed to use at least one iterative regression analysis technique to minimise the error function.

Preferably, the sensor includes a position determination means adapted to position the focal point of the focussing means on an outer boundary of a fat layer.

Preferably, the position determination means may be a laser sensor or tactile sensor.

Preferably, the sensor includes a means for orienting the sensor so that the microwave signals are transmitted through an outer surface of the fat substantially transverse to the outer surface of the fat.

According to another aspect of the invention there is provided a method of sensing the depth of fat in animal tissue including:
  generating and transmitting three or more focussed discrete narrow band microwave signals into the tissue;
  sensing the magnitude and phase of reflected microwave signals from the tissue;
  computing from the sensed magnitude and phase a value suitable for identification of the fat depth within the tissue.

Preferably, the method further includes the step of generating and transmitting microwave signals in the X-band.

Preferably, the method includes sensing the magnitude and phase of the reflected microwave signals using a six port reflectometer.

Preferably, the method includes focussing the microwave signals using a lens system.

Preferably, method further includes the step of computing the depth of fat by first computing the electrical length of the fat and computing the permittivity of the tissue in the focal area and computing the depth of fat from the electrical length divided by the square root of the permittivity.

Preferably, the method further includes the step of computing the electrical length ($d_e$) of the fat and permittivity ($\epsilon_r$) of the tissue by minimising the error function $$\sum_{i=1}^{N} \left[ \tan^2 \frac{\theta_i}{2} - \frac{1}{\epsilon_r} \tan^2 \left[ \frac{2\pi f_1 \cdot d_e}{c} \right] \right] = 0$$

or an equivalent, wherein $\theta_i$ is the phase of the received microwave signals, $f_1$ is the frequency of the received signals or frequency of the transmitted signal, c is speed of the microwave signals and N is the number of discrete narrow band signals transmitted into the tissue for the purposes of the measurement.

Preferably, the method further includes using at least one iterative regression analysis technique to minimise the error function.

Preferably, the method further includes the step of computing the reflection coefficient from the magnitude information from the six port reflectometer and computing the phase of the received microwave signals from the reflection coefficient.

Preferably, the method further includes the step of positioning the sensor so that a focal point of the microwave signals is positioned on an outer surface of the fat.

Further aspects of the present invention, which should be considered in all their novel aspects, may become apparent from the following description given by way of example and in reference to the accompanying drawings.

BRIEF DESCRIPTION OF PREFERRED EMBODIMENTS OF THE INVENTION

Figure 1:
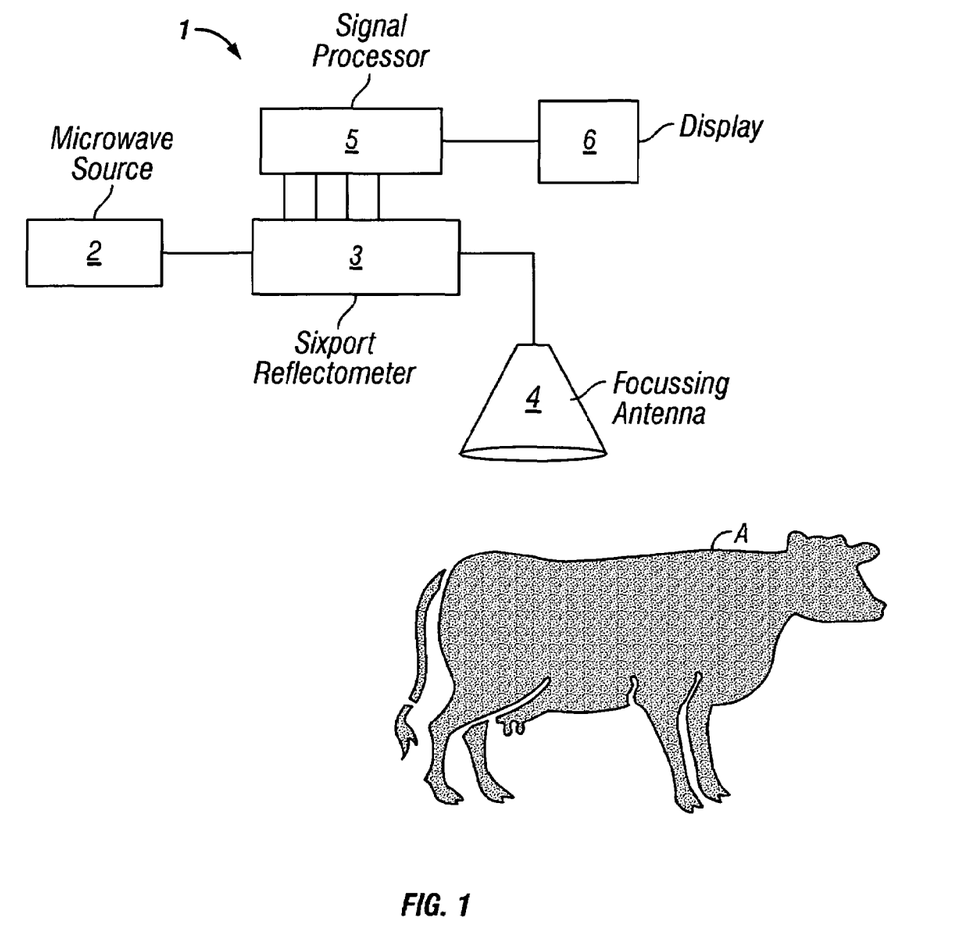
FIG. 1: shows a block diagram of a sensor according to one aspect of the invention.

Referring first to FIG. 1, a block diagram of a sensor 1, according to one aspect of the invention is shown. An animal carcass A, represented in FIG. 1 by a cow, which is to be measured to ascertain the depth of the fat layer F (see FIG. 2) is positioned near the sensor 1.

The sensor includes a microwave source 2 to generate microwave signals and communicate them to a sixport reflectometer 3 through a waveguide. The sixport reflectometer 3 communicates the microwave signals to a focussing antenna 4, which focuses the microwave signals onto a portion of the animal tissue.

Traditionally, the microwave source 2 would be used to generate a relatively wideband signal and the reflected energy would be analysed using Fourier Transform techniques. However, to reduce the effects of spurious reflections, provide a high resolution measurement and minimise the computational burden and associated cost and complexity, the present invention uses three discrete narrow-band signals. The preferred microwave signal is a simple carrier wave with no modulation. The carrier is swept over the desired frequency range, for example 500 MHz centred around 10 GHz.

In a preferred form of the invention, the microwave source 2 generates at least three signals in the X-band (approximately 10 GHz) spaced by approximately a few hundred megahertz. The X-band is used due to the lower componentry cost for microwave signals in this range at present. It will be appreciated by those skilled in the art that the resolution of the system may be increased by using higher frequencies, or alternatively, lower frequencies may be used with a corresponding reduction in resolution.

A suitable microwave source 2 for the purposes of the present invention, for example, is a YIG oscillator. A YIG oscillator provides sufficient power (10–1000 mW typically) to drive a sixport reflectometer (see herein below). A low pass filter may be used to reduce the presence of second harmonic in the signal as required. Attenuation of the second harmonic to 25 dB down from the fundamental frequency has been found sufficient for the purposes of the invention, although more or less attenuation may be used depending on the specific requirements for the system as may be readily determined by those skilled in the art.

Figure 3:
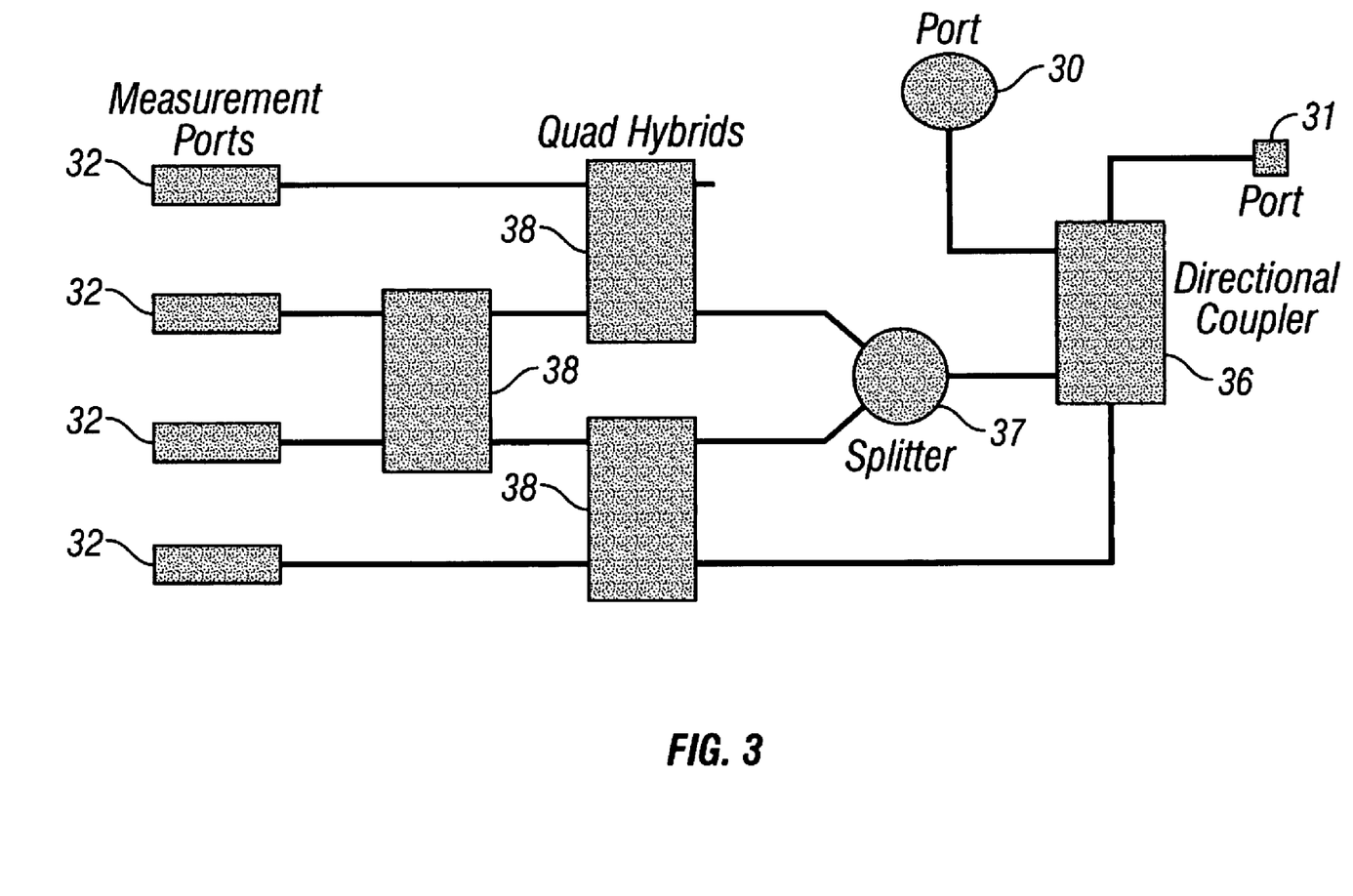
FIG. 3: shows a block diagram of a six-port reflectometer.

The microwave signals generated by the microwave source 2 are communicated through a waveguide to a sixport reflectometer 3. The sixport reflectometer 3 allows measurements to be taken of both the magnitude and phase of the received reflected microwave energy. FIG. 3 shows a block diagram of a sixport reflectometer 3 suitable for use for the purposes of the present invention. The sixport reflectometer 3 receives the microwave signals from the microwave source 2 at port 30, transmits and receives microwave signals to and from the animal carcass A at port 31 and the four measurement ports 32 to 35 provide voltage signals to the signal processor 5. The signal processor 5 then evaluates the magnitude and phase of the reflections. The sixport reflectometer 3 includes a directional coupler 36, a splitter 37 and three quad hybrids 38 to simulate a transmission line within the sixport reflectometer 3.

A calibration procedure to define the parameters and reference plane of the sixport reflectometer 3 is required before the sixport reflectometer 3 provides signals at the measurement ports 32 to 35 that can be used to accurately determine the reflection coefficient. Persons skilled in the art will appreciate that any calibration process suitable for calibrating portable microwave sensors may be used. However, by way of example, calibration may be achieved by applying a known standard to the reference plane or focal point of the sensor 1. A suitable standard is a movable short-circuit, which, when prompted by calibration software in a controller, is moved to one of four unique lengths and the measurements used to identify the parameters of the sixport reflectometer along with the position of the reference plane. The calibration process may be incorporated into the measurement process as a precursor to obtaining a measurement of the fat depth.

More particularly, in a focused system, such as the sensor 1 of the present invention, if a shorting plate is moved in range along the primary axis and if one assumes plane waves, the amplitude of the reflected wave will change. Thus we can write that the loci of $\Gamma_m$ will be $$\Gamma_m = \frac{\frac{A}{1+\alpha K\eta} \cdot \Gamma e^{-j2K\eta} + B}{\frac{C e^{-j2K\eta}}{1+\alpha K\eta} + 1} \qquad 1$$

and the loci is not a circle. In equation 1, $\Gamma_m$ is the measured reflection coefficient; $\Gamma$ is the reflection coefficient of the short circuit plate, $\Gamma=-1$; A, B and C are the normal bilinear constants and are complex; $\eta$ is the shift in range from some arbitrary reference point; K is the free space wave number; and $\alpha$ is a real constant. We have here assumed that as the shorting plate moves away from the focal point, the incident Poynting vector reduces as $1/\eta 2$.

In principle, we also need to account for the additional phase shift due to a converging or diverging beam, when measurements are made along the primary axis. Initially, however, we will ignore this and also make the assumption that the depth of field is large enough such that $\alpha \approx 0$, then equation 1 reduces to a bilinear transform shown in equation 2.

$$\Gamma_m = \frac{A\Gamma e^{-j2K\eta} + 1}{C\Gamma e^{-j2K\eta} + 1} \qquad 2$$

It is now sufficient to have the shorting plate at 3 positions, such that the ($\Gamma e^{-jK\eta_i}$) is spaced approximately uniformly along the unit circle. A, B and C are then evaluated in the normal way for each frequency.

The sensor 1 is calibrated using the method described above at the focal point or beam waist (the reference plane). In use, the sensor is located and oriented so that the beam waist is at the air/fat boundary. Therefore, the fat/muscle boundary may be considered as the only substantial reflector.

Alternative measurement devices to the sixport reflectometer 3 may be used. For example, a vector network analyser may be used. However, the cost, size, portability and simplicity of using of a sixport reflectometer 3 in combination with a signal processor 5 makes the sixport reflectometer 3 the preferred measurement device. Also, multi-port systems may alternatively be used, but these require an increased computational burden and a sixport reflectometer has been found to provide sufficient accuracy.

Figure 2:
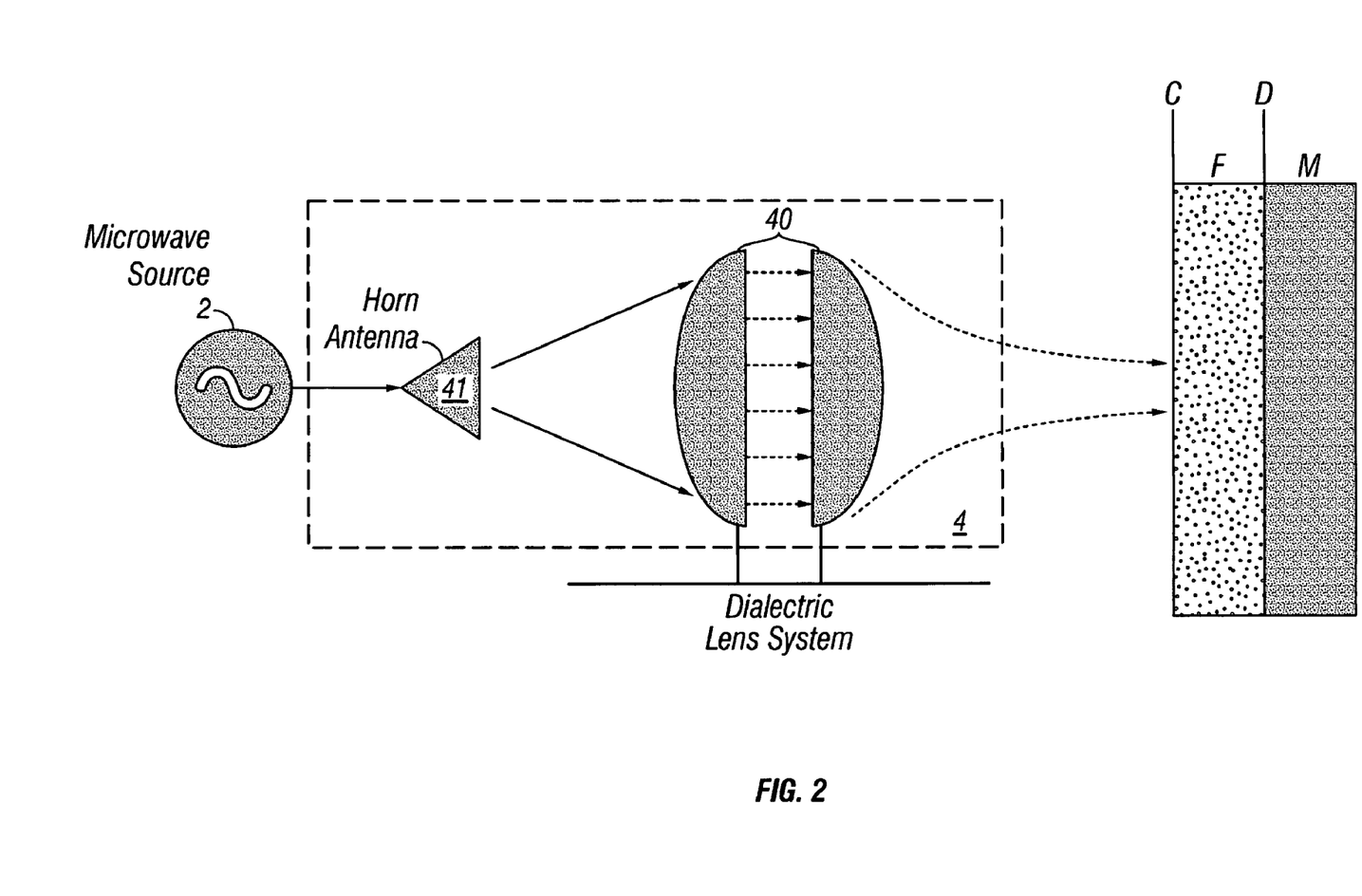
FIG. 2: shows a schematic representation of an antenna and animal carcass according to one aspect of the invention.

The antenna 4 is connected to port 31 through a waveguide. A focussing antenna 4 is used to reduce or eliminate the effects of off-axis spurious reflections from adjacent scatterers. Referring to FIG. 2, which shows a schematic representation of an antenna 4, a suitable antenna 4 may be constructed from dielectric lens system 40 illuminated using a standard horn antenna 41. The design of the dielectric lens system 40 may be selected according to the requirements of the system, but preferably the spot size at the focal point should be minimised to provide the highest resolution and corresponding highest accuracy measurements. A suitable spot size may, for example, be 30 mm. Other focussing antennas may be used depending on the specific requirements of the sensor 1 including, but not limited to reflectors, phased arrays and synthetic aperture methods. An integrated and rugged focusing system 4 is preferable to provide a robust sensor 1.

In use, the microwave signals reflected from the fat to muscle boundary, referenced D in FIG. 2 and from other minor reflections are detected. These reflections are collected by the focussing antenna 4 and fed back to the sixport reflectometer 3. This affects the standing wave within the sixport reflectometer 3, resulting in variations in the four voltage signals at the measurement ports 32–35. The four voltage signals are connected to a signal processor 5 for computation of the fat depth.

At least three measurements are taken at 3 different frequencies in the X-band, the measurements separated by a few hundred megahertz. The separation of the frequencies may be varied to influence the accuracy of the layer measurement, with a wider frequency range tending to generate more accurate measurements, but this needs to be traded off against increased variation in focal spot size, which decreases accuracy.

To obtain a measurement after the sensor 1 has been calibrated, the magnitude of the four voltages from the ports 32 to 35 are measured and the ratio of each port voltage to port 35 computed by the signal processor 5. The magnitude of the reflection coefficient is then determined from equation 3:

$$\Gamma = \frac{\sum_{i=3}^{6}(F_i + jG_i)p_i}{1 + \sum_{i=3}^{5} H_i p_i} \qquad 3$$

where the F,G,H are coefficients determined by the sixport calibration for each of the measurement ports and p is the voltage ratio of each port to port 35. Next, the reflection coefficient is modified from $\Gamma$ to $\Gamma_m$ (to move reference plane through the sensor to the air fat boundary), where:

$$\Gamma_m = \frac{A\Gamma e^{-j2K\eta} + 1}{C\Gamma e^{-j2K\eta} + 1} \qquad 4$$

As equation 4 is equivalent to equation 2, coefficients A and C are determined by the calibration process of moving a shorting plate through 3 positions with one being the focal point.

$\theta$ is then determined from the reflection coefficient $\Gamma_m$ using equation 5:

$$\Gamma_m = 1 \cdot e^{j\theta} \qquad 5$$

Once $\theta$ is known, it is possible to minimise the error function (i.e. minimise the sum of the difference between the value of the sum function in equation 6 and zero over all measurement frequencies) shown in equation 6:

$$\sum_{i=1}^{N}\left[\tan^2\frac{\theta_i}{2} - \frac{1}{\varepsilon_r}\tan^2\left[\frac{2\pi f_1 \cdot d_e}{c}\right]\right] = 0 \qquad 6$$

Where N is the number of frequency points ($N \geq 3$), $\theta_1$ is the phase of the reflection coefficient and $f_1$ is the frequency of the microwave signal, either as measured from the received signal or preferably, the value of the frequency of the signal as transmitted is used (they are equivalent). The error function of equation 6 may be minimised using an iterative process to yield the electrical length $d_e$ and permittivity $\varepsilon_r$ for at least three frequencies (i=3). Equation 6 can be derived from Fresnel's equations with an angle of incidence of zero, a derivation is shown below.

The starting point is Fresnel's equations for the reflection coefficient of a plane wave incident on the target medium backed by a short current can be written down as:

$$\Gamma_{\perp} = \frac{j\mu_r\cos\theta_i\tan\left[k_d \cdot (\mu_r\varepsilon_r - \sin^2\theta_i)^{\frac{1}{2}}\right] - (\mu_r\varepsilon_r - \sin^2\theta_i)^{\frac{1}{2}}}{j\mu_r\cos\theta_i\tan\left[k_d \cdot (\mu_r\varepsilon_r - \sin^2\theta_i)^{\frac{1}{2}}\right] + (\mu_r\varepsilon_r - \sin^2\theta_i)^{\frac{1}{2}}} \qquad 7$$

with $f_i = 0$ and $\mu_r = 1$. Then the reflection coefficient $\Gamma$ at die reference plane of the air-fat interface is $$\Gamma = \frac{\frac{j}{\sqrt{\varepsilon_r}}\tan kd\sqrt{\varepsilon_r} - 1}{\frac{j}{\sqrt{\varepsilon_r}}\tan kd\sqrt{\varepsilon_r} + 1} \qquad 7.1$$

Initially we assume that the target medium is loss free, then $$\Gamma = 1 \cdot e^{j\theta} \qquad 7.2$$

where, $$\theta = 2\tan^{-1}\left[\frac{-j}{\sqrt{\varepsilon_r}}\tan kd\sqrt{\varepsilon_r}\right] \text{ or,} \qquad 7.3$$

$$\tan\frac{\theta}{2} = \frac{-j}{\sqrt{\varepsilon_r}}\tan kd\sqrt{\varepsilon_r} \text{ Now as} \qquad 7.4$$

$$\Gamma = u + jv \text{ we have immediately} \qquad 7.5$$

-continued

$$\frac{-j}{\sqrt{\varepsilon_r}}\tan kd\sqrt{\varepsilon_r} = -\left[\left(\frac{u}{v}\right) \pm \sqrt{\left(\frac{u}{v}\right)^2 + 1}\right] \text{ where} \qquad 7.6$$

$$k = \frac{2\pi}{\lambda} = \frac{2\pi f}{c}$$

We note from (7.3) that $\varepsilon_r = 1$, then $$\theta = 2kd \qquad 7.7$$

and the phase change is linear with K. However, as $\varepsilon_r \neq 1$ in the target medium, determining the electrical length $d_e = d \cdot \sqrt{\varepsilon_r}$ from any one or two frequency measurements, will be in error. To evaluate the electrical length $d_e$, we need to sweep over a range of frequencies. The measured reflections after calibration of the instrument will then appear, with fixed frequency steps, as $\Gamma$ points as a function of frequency $\Gamma$ points as a function of frequency. Note that the points are not spaced equally, as $\varepsilon_r \neq 1$. From (7.6) we note that when $V \to 0$, then $$d_e = d\sqrt{\varepsilon_r} = \frac{(n+1)}{2} \cdot \frac{c}{f_0} \text{ if } \mu < 0 \text{ or} \qquad 7.8$$

$$d_e = d\sqrt{\varepsilon_r} = \frac{(2n+1)}{4} \cdot \frac{c}{f_0} \text{ if } \mu > 0, \text{ where n is an integer.} \qquad 7.9$$

Thus the electrical length $d_e$ is accurately determined, by simply calculating the frequency $f_0$ at which $V \to 0$. This is done by interpolation between 2 points nearest to $V \to 0$. Now we consider when $\mu \to 0$, then $$\frac{-j}{\sqrt{\varepsilon_r}}\tan kd\sqrt{\varepsilon_r} = 1 \text{ or} \qquad 7.10$$

$$\varepsilon_r = \tan^2\left[\frac{2\pi f_1 \cdot d_e}{c}\right] \qquad 7.11$$

where $f_i$ is the frequency at which $\mu \to 0$. It turns out though that it is better to minimise the error function.

$$\sum_{i=1}^{N}\left[\tan^2\frac{\theta_i}{2} - \frac{1}{\varepsilon_r}\tan^2\left[\frac{2\pi f_1 \cdot d_e}{c}\right]\right] = 0 \qquad 7.12$$

for $\varepsilon_r \geq 1$, where N is the number of frequency points and $f_i$ are the measurement frequency points. The error function in equation 7.12 is minimised for example using regression analysis with $\epsilon_r$ and $d_e$ as the variables.

It will be appreciated by those skilled in the art that the above equation may be manipulated into any number of alternative forms, which may be used in conjunction with a corresponding computational process achieves the same or substantially the same values as minimising the error function in equation 6. For example, the trigonometric functions $\tan^2()$ may be substituted for an equivalent and assumptions may be incorporated regarding approximately equal relationships to form new equations. This type of manipulation of mathematical relationships is well known in the art and widely used. Thus, any equivalent or substantially equivalent forms of equation 6 which may be identified, for example, to reduce computational burden, reduce computational time or make use of existing algorithms in the signal processor 5 are intended to fall within the scope of this invention.

Once $d_e$ and $\epsilon_r$ are known, the depth, d of the fat is determined as the electrical length divided by the square root of the permittivity. The depth may then be displayed on the display 6 or communicated elsewhere for subsequent use and or storage. For example, wireless communication could be used to communicate the result of each measurement to a central database.

It will be appreciated that the above computations to find the depth of the fat from the four voltage signals from the sixport reflectometer 3 may be easily implemented using a signal processor or other suitable processing means. However, a signal processor is preferred to maximise the speed of response of the sensor 1.

Thus, to obtain measurements of the fat depth, the sensor 1 is located near the animal carcass 2 and oriented so that the microwave signals are transmitted substantially perpendicularly to the air/fat interface or boundary. The sensor 1 can either be static or moved around the carcass A, for example on a robotic arm (not shown). Keeping the air/fat interface at the focal point of the lens system 40 is achieved by the use of a suitable range sensor, for example a laser or tactile sensor (not shown). Suitable devices for controlling the movement and positioning of the sensor 1 are well known in the art and therefore are not described herein. It is envisaged that for scanning over the animal carcass A, an automated device such as a robotic arm may be required to maintain the required accuracy, whereas for a single measurement at a specific point on the animal carcass 2, the sensor 1 could be positioned manually.

Where in the foregoing description, reference has been made to specific components or integers of the invention having known equivalents then such equivalents are herein incorporated as if individually set forth.

Although this invention has been described by way of example and with reference to possible embodiments thereof, it is to be understood that modifications or improvements may be made thereto without departing from the scope of the invention as defined in the appended claims.

What is claimed is:

1. A non-invasive sensor suitable for measuring the depth of fat in tissue, the sensor including:
   microwave signal generation and transmission means adapted to generate and transmit microwave signals into the tissue;
   focussing means adapted to focus the microwave signals onto a predetermined focal point;
   control means adapted to control the microwave signal generation and transmission means to transmit, in use, at least three discrete narrow band microwave signals into the tissue;
   receiving means adapted to receive reflected microwave signals from the tissue and provide magnitude and phase information of the reflected microwave signals; and
   processing means for receiving the magnitude and phase information provided by the receiving means and computing a value suitable for identification of the fat depth within the tissue.

2. A non-invasive sensor as claimed in claim 1, wherein the microwave generation and transmission means generates and transmits microwave signals in the X-band.

3. A non-invasive sensor as claimed in claim 1, wherein the receiving means includes a six port reflectometer.

4. A non-invasive sensor as claimed in claim 1, wherein the focussing means includes a lens system.

5. A non-invasive sensor as claimed in claim 1, wherein the processing means is programmed to compute the reflection coefficient of received microwave signals.

6. A non-invasive sensor as claimed in claim 5, wherein the processing means is programmed to compute the phase of the received microwave signals from the reflection coefficient.

7. A non-invasive sensor as claimed in claim 1 wherein the processing means is programmed to compute the depth of fat by first computing the electrical length of the fat and computing the permittivity of the tissue at the focal point, and computing the depth of fat from the electrical length divided by the square root of the permittivity.

8. A non-invasive sensor as claimed in claim 7, wherein the processing means is programmed to compute the electrical length ($d_e$) of the fat and permittivity ($\epsilon_r$) of the tissue by computing the values of electrical length and permittivity that minimise the error function $$\sum_{i=1}^{N}\left[\tan^2\frac{\theta_i}{2} - \frac{1}{\epsilon_r}\tan^2\left[\frac{2\pi f_1 \cdot d_e}{c}\right]\right] = 0$$

or is programmed to perform an equivalent computation, wherein $\theta_i$ is the phase of the received microwave signals, $f_1$ is the frequency of the received signals or frequency of the transmitted signal, c is speed of the microwave signals and N is the number of discrete narrow band signals transmitted into the tissue for the purposes of the measurement.

9. A non-invasive sensor as claimed in claim 8, wherein the processing means is programmed to compute the reflection coefficient of reflected microwave signals from the magnitude information from the receiving means and compute the phase of the received microwave signals from the reflection coefficient.

10. A non-invasive sensor as claimed in claim 8, wherein the processing means is programmed to use at least one iterative regression analysis technique to minimise the error function.

11. A non-invasive sensor as claimed in claim 1, wherein, the sensor includes a positioning means adapted to position the focal point of the focussing means on an outer boundary of a fat layer.

12. A non-invasive sensor as claimed in claim 11, wherein the position determination means is a laser sensor or a tactile sensor.

13. A non-invasive sensor as claimed in claim 1, wherein, the sensor includes a means for orienting the sensor so that the microwave signals are transmitted through an outer surface of the fat substantially transverse to the outer surface of the fat.

14. A method of sensing the depth of fat in tissue including:
generating and transmitting three or more focussed discrete narrow band microwave signals into the tissue;
sensing the magnitude and phase of reflected microwave signals from the tissue;
computing from the sensed magnitude and phase a value suitable for identification of the fat depth within the tissue.

15. The method of claim 14, wherein the method further includes the step of generating and transmitting microwave signals in the X-band.

16. The method of claim 14 including sensing the magnitude and phase of the reflected microwave signals using a six port reflectometer.

17. The method of claim 14 including focussing the microwave signals using a lens system.

18. The method of claim 14, wherein the method further includes the step of computing the depth of fat by first computing the electrical length of the fat and computing the permittivity of the tissue at the focal point, and computing the depth of fat from the electrical length divided by the square root of the permittivity.

19. The method of claim 18, wherein the method further includes the step of computing the electrical length ($d_e$) of the fat and permittivity ($\epsilon_r$) of the tissue by minimising the error function $$\sum_{i=1}^{N} \left[ \tan^2 \frac{\theta_i}{2} - \frac{1}{\epsilon_r} \tan^2 \left[ \frac{2\pi f_1 \cdot d_e}{c} \right] \right] = 0$$

or an equivalent, wherein $\theta_i$ is the phase of the received microwave signals, $f_1$ is the frequency of the received signals or frequency of the transmitted signal, c is speed of the microwave signals and N is the number of discrete narrow band signals transmitted into the tissue for the purposes of the measurement.

20. The method of claim 19, wherein the method further includes the step of computing the reflection coefficient of reflected microwave signals from the sensed magnitude and computing the phase of the received microwave signals from the reflection coefficient.

21. The method of claim 19, further including using at least one iterative regression analysis technique to minimise the error function.

22. The method of claim 14, wherein the step of transmitting three or more focussed discrete narrow band microwaves signals into the tissue includes focussing the narrow band microwave signals on to a focal point positioned on an outer surface of the fat.

* * * * *

UNITED STATES PATENT AND TRADEMARK OFFICE
CERTIFICATE OF CORRECTION

PATENT NO. : 7,089,047 B2 Page 1 of 1
APPLICATION NO. : 10/173226
DATED : August 8, 2006
INVENTOR(S) : Wayne Stephen Holmes It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (233) days Delete the phrase "by 233 days" and insert -- by 398 days --

Signed and Sealed this

Twenty-ninth Day of April, 2008

JON W. DUDAS
*Director of the United States Patent and Trademark Office*